US00PP32890P2

(12) United States Plant Patent
Verduin

(10) Patent No.: US PP32,890 P2
(45) Date of Patent: Mar. 9, 2021

(54) ***ASTILBE* PLANT NAMED 'WONDEFUL DAY'**

(50) Latin Name: *Astilbe arendsii*
Varietal Denomination: Wonderful Day

(71) Applicant: Harrie Verduin, Heemskerk (NL)

(72) Inventor: Harrie Verduin, Heemskerk (NL)

(73) Assignee: COMPASS PLANTS B.V., Hillegom (NL)

( * ) Notice: Subject to any disclaimer, the term of this patent is extended or adjusted under 35 U.S.C. 154(b) by 0 days.

(21) Appl. No.: 16/873,614

(22) Filed: May 21, 2020

(51) Int. Cl.
*A01H 5/02* (2018.01)
*A01H 6/80* (2018.01)

(52) U.S. Cl.
USPC ..... Plt./407
CPC ..... *A01H 6/80* (2018.05)

(58) Field of Classification Search
USPC ..... Plt./407
CPC ..... A01H 6/80
See application file for complete search history.

(56) References Cited

PUBLICATIONS

UPOV hit on *Astilbe* plant named, 'Wonderful Day', QZ PBR 20200352, filed Feb. 1, 2020.*

* cited by examiner

*Primary Examiner* — Anne Marie Grunberg
(74) *Attorney, Agent, or Firm* — C. Anne Whealy

(57) ABSTRACT

A new and distinct cultivar of *Astilbe* plant named 'Wonderful Day', characterized by its compact, broadly upright and mounding plant habit; moderately vigorous to vigorous growth habit; dense and bushy appearance; dark green-colored leaves; freely and uniformly flowering habit; dark pink-colored flowers on strong, tall and upright peduncles; and good container and garden performance.

2 Drawing Sheets

Figure 1:
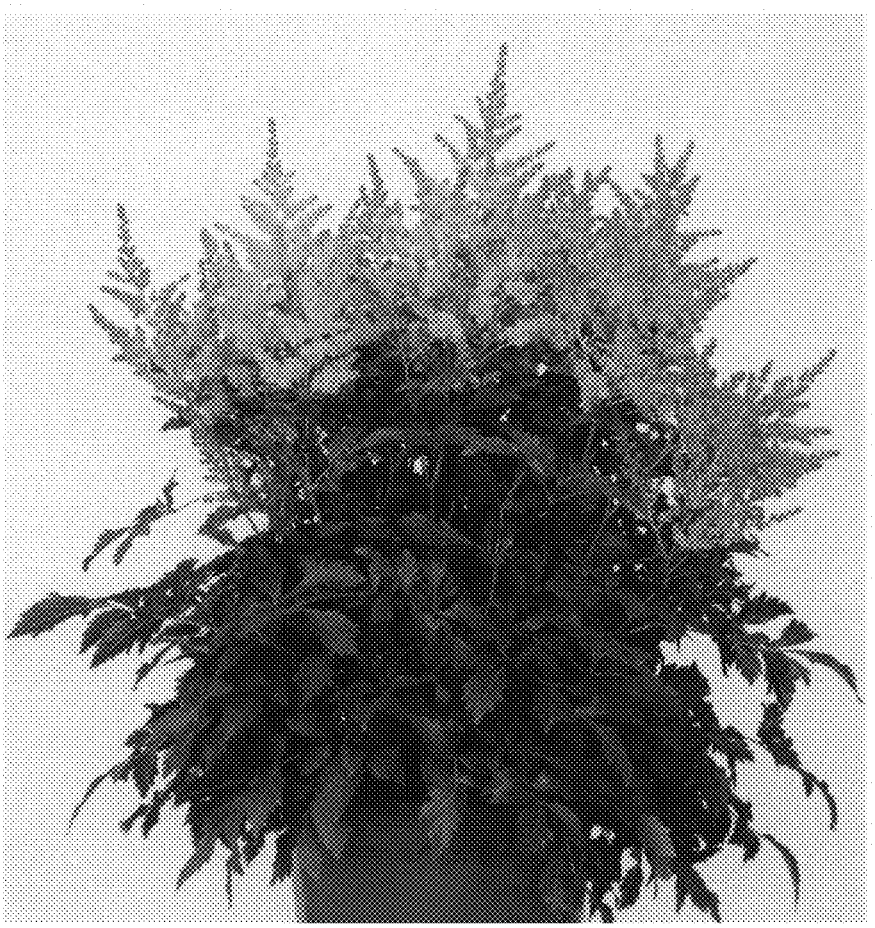

Botanical designation: *Astilbe arendsii.*
Cultivar denomination: 'WONDERFUL DAY'.

CROSS-REFERENCE TO A RELATED APPLICATION AND STATEMENT REGARDING PRIOR DISCLOSURES BY INVENTOR/APPLICANT

This application claims priority to a European Community Plant Breeders' Rights application filed on Feb. 1, 2020, application number 20200352. There have been no offers for sale anywhere in the world prior to the effective filing date of this Application and no accessibility to one of ordinary skill in the art could have been derived from the printed Plant Breeder's Rights documents.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor. Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Astilbe*, botanically known as *Astilbe arendsii* and hereinafter referred to by the name 'Wonderful Day'.

The new *Astilbe* plant is a product of a planned breeding program conducted by the Inventor in Heemskerk, The Netherlands. The objective of the breeding program was to create new uniform and freely flowering *Astilbe* plants with attractive leaf and flower coloration.

The new *Astilbe* plant originated from a cross-pollination in 2013 in Heemskerk, The Netherlands, of two unidentified *Astilbe arendsii* seedling selections. The new *Astilbe* plant was discovered and selected by the Inventor as a single flowering plant from within the progeny of the stated cross-pollination in a controlled greenhouse environment in Heemskerk, The Netherlands during the summer of 2015.

Asexual reproduction of the new *Astilbe* plant by vegetative divisions in a controlled nursery environment in Heemskerk, The Netherlands since December, 2015, has shown that the unique features of this new *Astilbe* plant are stable and reproduced true to type in successive generations.

SUMMARY OF THE INVENTION

Plants of the new *Astilbe* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Wonderful Day'. These characteristics in combination distinguish 'Wonderful Day' as a new and distinct *Astilbe* plant:

1. Compact, broadly upright and mounding plant habit.
2. Moderately vigorous to vigorous growth habit.
3. Dense and bushy appearance.
4. Dark green-colored leaves.
5. Freely and uniformly flowering habit.

6. Dark pink-colored flowers on strong, tall and upright peduncles.
7. Good container and garden performance.

Plants of the new *Astilbe* differ primarily from plants of the parent selections in plant habit as plants of the new *Astilbe* are more compact and denser than plants of the parent selections. In addition, inflorescences of plants of the new *Astilbe* are longer than inflorescences of plants of the parent selections.

Plants of the new *Astilbe* can be compared to plants of *Astilbe arendsii* 'Verspink', disclosed in U.S. Plant Pat. No. 19,841. In side-by-side comparisons, plants of the new *Astilbe* and 'Verspink' differ primarily in the following characteristics:

1. Inflorescences of plants of the new *Astilbe* are smaller than inflorescences of plants of 'Verspink'.
2. Flowers of plants of the new *Astilbe* are more purplish pink in color than flowers of plants of 'Verspink' which are more reddish pink in color.

Plants of the new *Astilbe* can be compared to plants of *Astilbe arendsii* 'Europa', not patented. In side-by-side comparisons, plants of the new *Astilbe* and 'Europa' differ primarily in the following characteristics:

1. Plants of the new *Astilbe* are more compact than plants of 'Europa'.
2. Inflorescences of plants of the new *Astilbe* are smaller than inflorescences of plants of 'Europa'.
3. Flowers of plants of the new *Astilbe* are dark pink in color whereas flowers of plants of 'Europa' are brighter pink in color.

BRIEF DESCRIPTION OF THE PHOTOGRAPHS

The accompanying colored photographs illustrate the overall appearance of the new *Astilbe* plant showing the colors as true as it is reasonably possible to obtain in colored reproductions of this type. Colors in the photographs may differ slightly from the color values cited in the detailed botanical description which accurately describe the colors of the new *Astilbe* plant.

The photograph on the first sheet (FIG. 1 of 2) is a side perspective view of a typical flowering plant of 'Wonderful Day' grown in a container.

Figure 2:
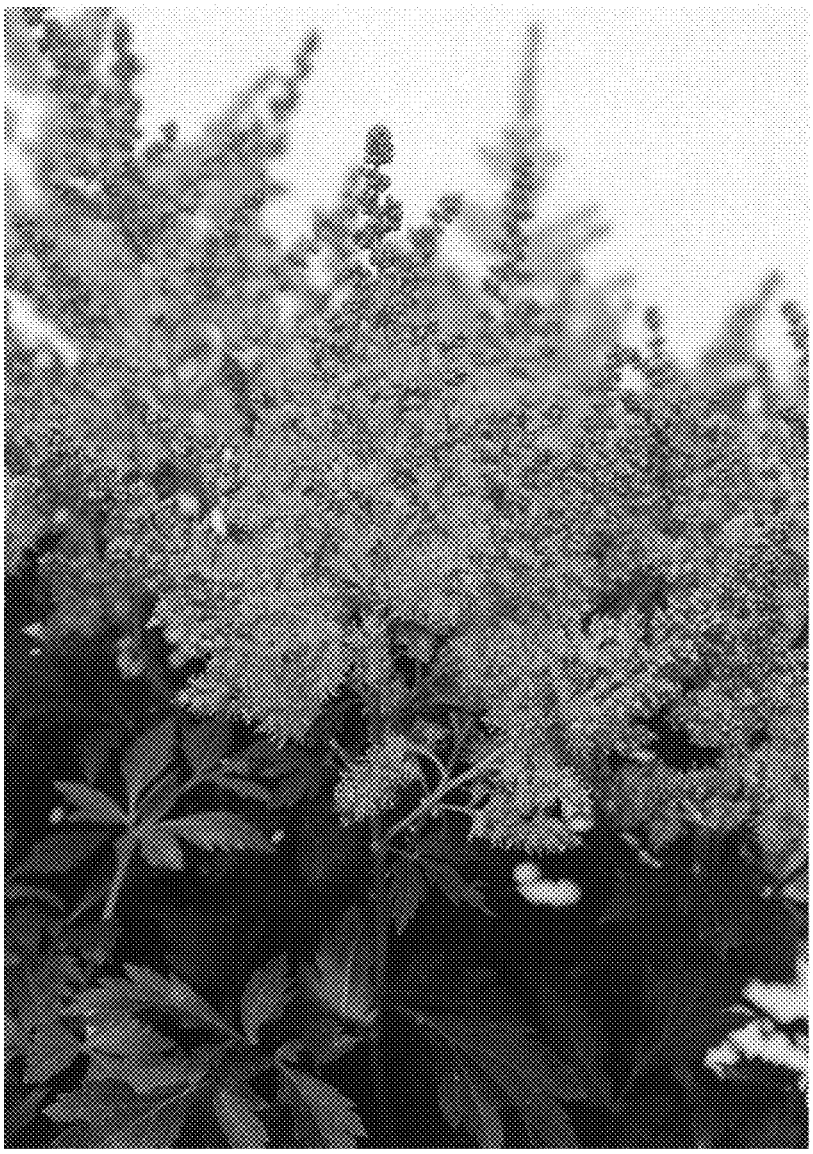

The photograph on the second sheet (FIG. 2 of 2) is a close-up view of typical inflorescences of 'Wonderful Day'.

DETAILED BOTANICAL DESCRIPTION

The aforementioned photographs and following observations, measurements and values describe plants grown during the summer in 19-cm containers in an outdoor nursery in Heemskerk, The Netherlands and under cultural practices typical of commercial *Astilbe* production. During the production of the plants, day temperatures ranged from 20° C. to 40° C. and night temperatures ranged from 8° C. to 24° C. Plants were one year old when the photographs and description were taken. In the following description, color references are made to The Royal Horticultural Society Colour Chart, 2015 Edition, except where general terms of ordinary dictionary significance are used.

Botanical classification: *Astilbe arendsii* 'Wonderful Day'.

Parentage:

*Female, or seed, parent*.—Unidentified *Astilbe arendsii* seedling selection, not patented.

*Male, or pollen, parent*.—Unidentified *Astilbe arendsii* seedling selection, not patented.

Propagation:

*Type*.—By vegetative divisions.

*Time to initiate roots*.—About three weeks at temperatures about 20° C.

*Root description*.—Thick, fleshy; typically brown in color, actual color of the roots is dependent on substrate composition, water quality, fertilizer type and formulation.

*Rooting habit*.—Freely branching; dense.

Plant description:

*Plant form and growth habit*.—Herbaceous perennial; compact, broadly upright and mounding plant form with inflorescences held above the foliar plane; flowering stems and leaves basal; freely flowering with numerous basal branches developing per plant, dense and bushy; moderately vigorous to vigorous growth habit; and freely and uniformly flowering habit.

*Growth rate*.—Moderately rapid; from divisions, about three months are required to produce fully-grown flowering plants in containers.

*Plant height* (*soil level to top of foliar plane*).—About 27.2 cm.

*Plant height* (*soil level to top of inflorescences*).—About 40.2 cm.

*Plant width* (*spread*).—About 41.1 cm.

*Stem description*.—Length: About 18.4 cm. Diameter: About 3 mm. Internode length: About 5.8 cm. Strength: Strong. Aspect: Erect to about 15° from vertical. Texture and luster: Sparsely pubescent; moderately glossy. Color, developing: Close to 144C. Color, developed: Close to 144B.

Leaf description:

*Arrangement*.—Alternate; biternately compound; on average, about 22 leaflets per leaf.

*Leaf length* (*excluding petiole*).—About 13.1 cm.

*Leaf width*.—About 12.3 cm.

*Terminal leaflet length*.—About 5.3 cm.

*Terminal leaflet width*.—About 2.5 cm.

*Lateral leaflet length*.—About 3.7 cm.

*Lateral leaflet width*.—About 1.7 cm.

*Leaf shape, in outline*.—Broadly ovate to narrowly deltoid.

*Leaflet shape*.—Elliptic to narrowly ovate.

*Leaflet apex*.—Slightly apiculate to acuminate.

*Leaflet base*.—Attenuate to narrowly cuneate.

*Leaflet margin*.—Biserrate.

*Leaflet texture and luster, upper and lower surfaces*.—Sparsely pubescent; slightly glossy.

*Leaflet venation pattern*.—Pinnate.

*Leaflet color*.—Developing leaflets, upper surface: Close to 144A. Developing leaflets, lower surface: Close to 146C. Fully expanded leaflets, upper surface: Close to between NN137A and 147A; venation, close to 144A to 144B. Fully expanded leaflets, lower surface: Close to 147B; venation, close to 144C.

*Leaf petiole length*.—About 13.5 cm.

*Leaf petiole diameter*.—About 2 mm.

*Leaf and leaflet petiole strength*.—Strong.

*Leaf and leaflet petiole texture and luster, upper and lower surfaces*.—Sparsely pubescent; moderately glossy.

*Leaf and leaflet petiole color, upper surface*.—Close to 144A; at the nodes, close to 152B.

*Leaf and leaflet petiole color, lower surface*.—Close to 144A.

Flower description:

*Flower type and flowering habit*.—Single rotate flowers arranged on terminal compound panicles; flowers face upright, outward or downward depending on position on the inflorescence; panicles conical in shape; freely and uniformly flowering habit with about 2,000 flowers developing per inflorescence and about 40,000 flowers developing per plant during the flowering season.

*Fragrance*.—Faint; moldy-sweet and pleasant.

*Natural flowering season*.—Plants begin flowering about 13 weeks after planting; continuously flowering from late spring until late summer in The Netherlands.

*Postproduction longevity*.—Flowers last about ten days on the plant; flowers not persistent.

*Flower buds*.—Height: About 1.75 mm. Diameter: About 1.6 mm. Shape: Broadly elliptic to nearly spherical. Texture and luster: Smooth, glabrous; matte. Color: Sepals, close to 144B and petals, close to 65A.

*Inflorescence height*.—About 15.7 cm.

*Inflorescence diameter*.—About 12.7 cm.

*Flower diameter*.—About 4 mm.

*Flower depth*.—About 3 mm.

*Petals*.—Quantity per flower: Typically five in a single whorl. Length: About 3 mm. Width: About 0.6 mm. Shape: Oblanceolate. Apex: Obtuse. Base: Narrowly cuneate. Margin: Entire; not undulate. Texture and luster, upper and lower surfaces: Smooth, glabrous; matte. Color: Developing petals, upper and lower surfaces: Close to 75A. Fully expanded petals, upper and lower surfaces: Close to NN74D; with development, color becoming lighter than NN74D.

*Sepals*.—Quantity per flower: Typically five in a single whorl, lower 40% fused towards the base forming a campanulate-shaped calyx. Length: About 2 mm. Width: About 1 mm. Shape: Ovate. Apex: Bluntly acute. Base: Cuneate, fused. Margin: Entire. Texture and luster, upper and lower surfaces: Smooth, glabrous; matte. Color: Developing sepals, upper surface: Close to 145D; at the margins, close to 73D. Developing sepals, lower surface: Close to 145D; at the margins, close to 73C. Fully expanded sepals, upper and lower surfaces: Close to 150D; at the margins, close to 75D; colors do not change with development.

*Peduncles*.—Length: About 15.4 cm. Diameter: About 2 mm. Angle: Mostly erect. Strength: Strong. Texture and luster: Sparsely pubescent; moderately glossy. Color: Close to 146C.

*Pedicels*.—Length: About 1 mm. Diameter: About 0.5 mm. Angle: About 45° from peduncle axis. Strength: Moderately strong. Texture and luster: Moderately pubescent; matte. Color: Close to 63D.

*Reproductive organs*.—Stamens: Quantity per flower: Typically ten; anthers basifixed. Filament length: About 2 mm. Filament color: Close to 75D. Anther shape: Broadly ovate. Anther length: About 0.5 mm. Anther diameter: About 0.25 mm. Anther color: Close to 69A. Pollen amount: Scarce. Pollen color: Close to 156D. Pistils: Quantity per flower: Two. Pistil length: About 1.75 mm. Stigma diameter: About 0.1 mm. Stigma shape: Club-shaped. Stigma color: Close to 64D. Style length: About 1.5 mm. Style color: Close to 69A. Ovary color: Close to 69A.

*Seeds and fruits*.—To date, seed and fruit development have not been observed on plants of the new *Astilbe*.

Pathogen & pest resistance: To date, plants of the new *Astilbe* have not been noted to be resistant to pathogens and pests common to *Astilbe* plants.

Garden performance: Plants of the new *Astilbe* have been observed to have good garden performance and tolerate rain, wind, temperatures ranging from about −25° to 35° C. and to be suitable for USDA Hardiness Zones 5 through 10.

It is claimed:

1. A new and distinct *Astilbe* plant named 'Wonderful Day' as illustrated and described.

* * * * *